United States Patent [19]

Hall et al.

[11] Patent Number: 4,937,879
[45] Date of Patent: Jul. 3, 1990

[54] AUTOMATIC WELDING HELMET

[76] Inventors: David R. Hall, Box 4312, Enterprise, Fla. 32725; Mark Steele, 1913 Sheeler Oaks Dr., Apopka, Fla. 32703

[21] Appl. No.: 265,255

[22] Filed: Oct. 31, 1988

[51] Int. Cl.$^5$ .............................................. A61F 9/06
[52] U.S. Cl. ........................................... 2/8; 219/147
[58] Field of Search ............................... 2/8, 424, 6, 9; 219/147, 132

[56] References Cited

U.S. PATENT DOCUMENTS

| | | | |
|---|---|---|---|
| 2,471,719 | 5/1949 | Broffitt | 2/8 |
| 2,678,369 | 5/1954 | Van Hook | 219/147 |
| 3,096,430 | 7/1963 | Farr | 219/147 |
| 3,692,974 | 9/1972 | Thomason | 219/147 |
| 3,719,793 | 3/1973 | Finger | 2/147 |
| 3,792,226 | 2/1974 | Bush | 219/147 |
| 3,838,247 | 9/1974 | Finger | 2/8 X |
| 4,293,757 | 10/1981 | Niemi | 2/8 X |
| 4,571,741 | 2/1986 | Guillaumot | 2/8 |

FOREIGN PATENT DOCUMENTS

| | | | |
|---|---|---|---|
| 55-97883 | 7/1980 | Japan | 219/147 |
| 0671145 | 4/1952 | United Kingdom | 2/8 |

Primary Examiner—Peter Nerbun
Attorney, Agent, or Firm—Peter D. Keefe

[57] ABSTRACT

An automatic rotatable welding helmet for TIG and MIG electric arc welding systems having safety means preventing the arc cycle from commencing until the helmet is in the fully down position. An arc welding helmet is provided having a hood with eye shield, connected by pivoting means to an interior head band harness. The hood has an exteriorly mounted base supporting a bi-directional piston and cylinder mechanism which, under actuation by a source of compressed air, pushes against a cam connected at the pivot, resulting in rotation of the helmet from the fully open to the fully closed position, and vice versa. In operation, the welder presses a welding cycle activation switch which effects, through a control box, to deliver compressed air to one end of the cylinder, forcing the piston outward against the cam, thereby rotating the helmet. A safety switch mounted to the base, assures positive protection against the arc cycle being started until the helmet is in the fully down position. Release of the foot pedal deactivates the arc, and, via the control box, directs compressed air to the other end of the cylinder, opening the helmet.

6 Claims, 4 Drawing Sheets

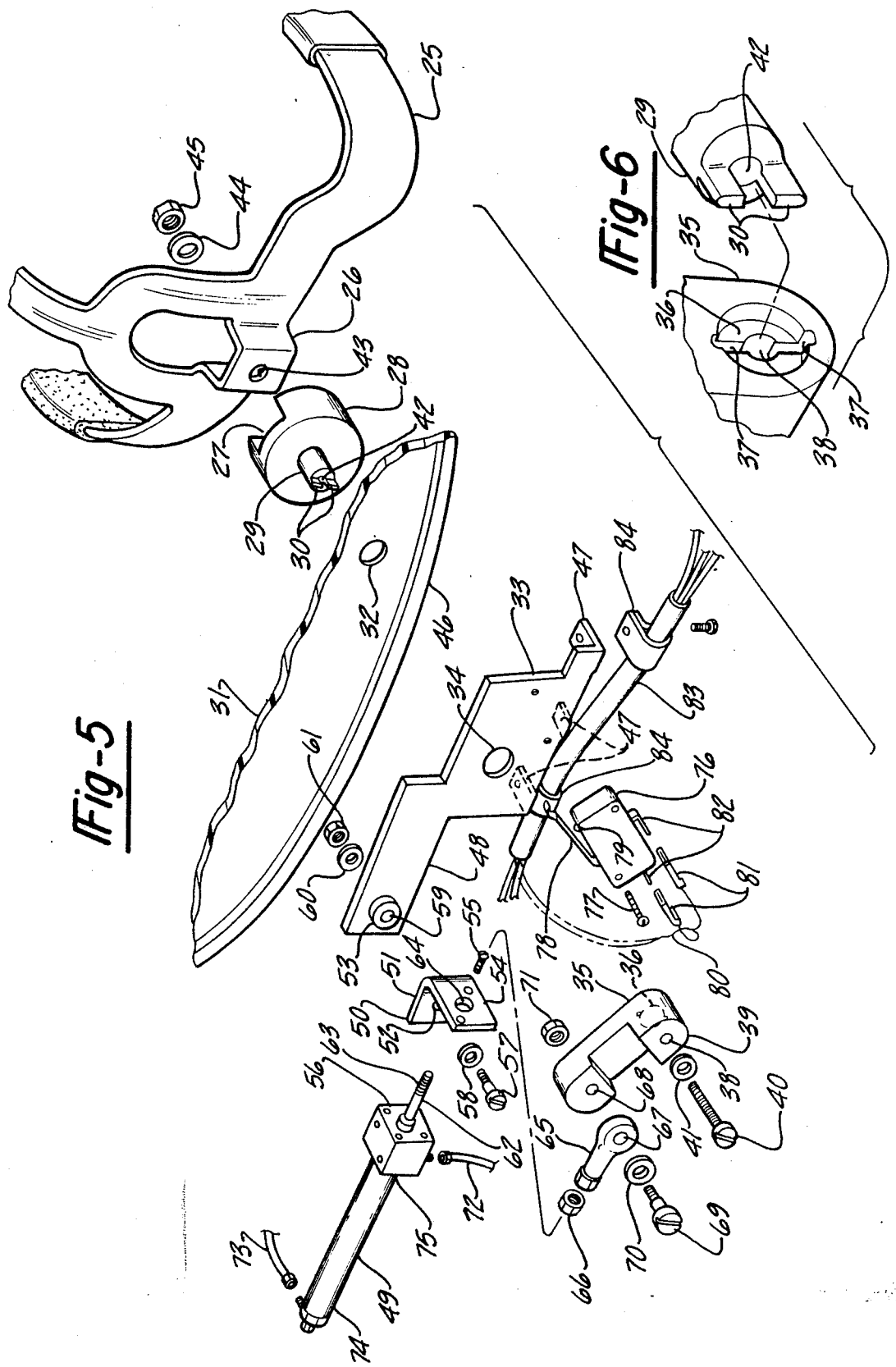

AUTOMATIC WELDING HELMET

BACKGROUND OF THE INVENTION

This invention relates to electric arc welding apparatus, more particularly to an automatic, rotatable welding helmet designed to greatly improve safety and protection of the welder, and at the same time aid in improving his working conditions and workmanship.

In the technology of electric arc welding, systems have been developed to provide an inert gas as a shielding agent around the metals being welded, in order to reduce atmospheric contamination which can reduce overall weld strength and performance. These have become known as Tungsten Inert-Gas, or TIG, and Metal Inert-Gas, or MIG. Both these sytems employ an arc welding circuit which includes a source of electric current, an electrode (in the case of TIG systems being non-consumable and in the case of MIG systems being consumable) and a welding cycle activation switch (in the case of TIG systems being a foot pedal and in the case of MIG systems being a hand trigger) which is used to regulate the inert gas flow and electric current, via a delay circuit, in such manner as to ensure that inert gas has surrounded the work piece before the arc may be struck.

The arc so produced is of an extreme intensity and covers the electromagnetic spectrum both above (ultraviolet) and below (infrared) the frequency of the visible region. These rays are extremely damaging to the eyes; even exposed skin surfaces may experience a sunburning effect as a result of an arc welding session. Consequently, protective means have developed over the years to assure that welders are not put at risk due to long term, intensive welding assignments. These include protective clothing, gloves and welding helmet. The helmet is particularly critical to the welder in terms of the need to cancel any harmful rays and generally protect the face from sparks. In order to achieve this result, opaque hoods which generally cover the face and neck areas are used, having light transmitting, face mounted shields for viewing incorporating very high attenuation characteristics, essentially cancelling all ultraviolet and infrared light and greatly reducing the intensity of transmitted visible light. As a consequence, these helmets, when worn by the welder, prevent him from seeing anything, since room light is insufficient in intensity to permit seeing outside the shield, until an arc is struck; yet these helmets must be worn in advance of striking an arc to prevent injury. This dichotomy has plagued the art since its inception.

Conventional practice among welders has been to position the electrode at the work piece, press the welding cycle activation switch, and, by utilizing a nod of the head, cause the helmet to lower over their face by means of a head band pivot arrangement common in the art. This involves a degree of chance that the arc may prematurely strike, or that the nodding action may cause misalignment of the electrode (which won't be known when the hood is down until the arc strikes and sufficient light permits the welder to see through the face plate).

In the prior art, attempts have been made to devise an automatic safety means to assure that a welder will not be accidentally exposed to the harmful rays of an electric arc. Patent 3,096,430 to Farr, is typical of these previous attempts. There, the face plate is rotatably mounted upon the hood so that it may be alternately moved up out of the way, permitting visual inspection of the job in ordinary room light, and down, thereby assuring that only filtered light reaches the welder's eyes. With the helmet fully down, the foot pedal switch used in TIG systems, or the hand trigger used in MIG systems, is utilized not only to signal to a relay in its usual function of starting the inert gas flow and subsequent current flow to the electrode, but also to signal introduction of compressed air into a piston-cylinder assembly mounted upon the helmet, activating rotary closure of the eye shield (not the hood itself) in advance of striking the arc. This, and previous solutions have failed to address the primary concern of welders: they wish to spend as little time under the hood as possible. Consequently, the present invention solves the need in the art to provide an automatic safety mechanism to prevent eye injury and concomitently minimize under hood time by providing an automatically activated rotatable welding helmet system.

It is, therefore, an object of the invention to provide an automatic safety welding helmet adaptable to existing TIG and MIG welding systems, that provides for minimum time that the welder must spend under the hood.

It is a further object of the invention to provide a fully automatic system utilizing an electrical safety circuit and air control system integrated as one system, having the advantage of a totally adjustable hands off capability.

It is still a further object of the invention to provide a safety system that protects the welder's eyes from harmful electric arc light rays by not allowing the arc cycle to commence until the helmet is in the fully down position.

It is yet a further object of the invention to provide a safety system which reduces welder neck and shoulder fatigue due to elimination of nodding motions used to lower conventional helmet hoods.

It is still a further object of the invention to provide a safety system for arc welding which improves workmanship by: (1) leaving both hands free to position the work piece and the electrode, (2) elimination of flinching at the moment that the arc strikes and higher level of concentration on the job at hand, since worry of accidental striking with the hood still raised is absent, and (3) better working conditions for the welder, since his vision is unrestricted and his personal comfort increased while the hood is up.

These, and additional objects, advantages, features, and benefits of the invention will become apparent from the following specification.

SUMMARY OF THE INVENTION

In the present invention, a rotatable welder's helmet is provided which is activated by means of compressed air in response to pressing of a welding cycle activation switch of the type commonly used in TIG and MIG arc welding systems, rotation to the fully down position being a prerequisite to commencement of cycling of the welding system and striking of an arc.

The invention generally comprises a conventionally configured arc welding helmet having a hood with eye shield and a head band harness having provision for articulating the hood about the harness, which is modified as follows: A base is connected exteriorly to the hood, attached to which is an air cylinder and bi-directional piston mechanism which in turn connects, through a piston shaft, to a cam which is itself attached to the head band harness. The hood is pivoted about an axis going through one end of the cam at one side thereof and via a frictional control at the other. A safety switch is also attached to the base in such manner that rotation about the cam will bias it to the "on" mode only when the hood is in the fully down position. This switch assures that the welding cycle can only commence and continue while the switch is biased "on", meaning an arc can strike only when the hood is fully down, effectively protecting the welder.

The invention is designed to adapt to existing TIG and MIG arc welding systems with a very minimum of modification. Such modifications are: incorporation of rotational activation means in the helmet, as described generally above, substitution of a double polarity switch for the single polarity spring biased welding system activation switch (which may have the form of a foot pedal or hand trigger), a source of compressed air (which is entirely unrelated to the inert gas system), a control box incorporating a solenoid activated spring biased air valve, air pressure regulators, system electrical activation switch, and associated wires, air hoses and related hardware.

In operation, depressing the spring biased welding system activation switch will cause the solenoid air valve to send compressed air into the cylinder, which will then cause the piston to move outward, in turn causing force to be applied to the cam, resulting in a rotation of the hood about the pivot point. When the hood fully closes over the welder's head, the safety switch is activated, closing the welding apparatus circuit and permitting the welding cycle to commence. Releasing the welding system activation switch, cuts power to the solenoid air valve, allowing for spring biased switching within said air valve of the compressed air to the other end of the cylinder, resulting in rotation of the hood upwards and interruption of the welding apparatus circuit not only at the welding system activation switch, but at the safety switch as well.

The control box provides for three user defined operational modes: (1) fully automatic operation, as described above, (2) manual operation of hood rotation, but with the safety switch still in the electrical circuit, and (3) fully manual operation, in which the hood is rotated manually and the safety switch is out of the circuit.

BRIEF DESCRIPTION OF THE DRAWINGS

FIG. 5 is an exploded perspective view of the helmet rotation actuation means.

FIG. 6 is a detail view of the interconnection structure between the stationary head band structure and the rotational actuation means, as depicted in FIG. 5.

DETAILED DESCRIPTION OF THE PREFERRED EMBODIMENT

I. Overview of the Invention

Figure 1:
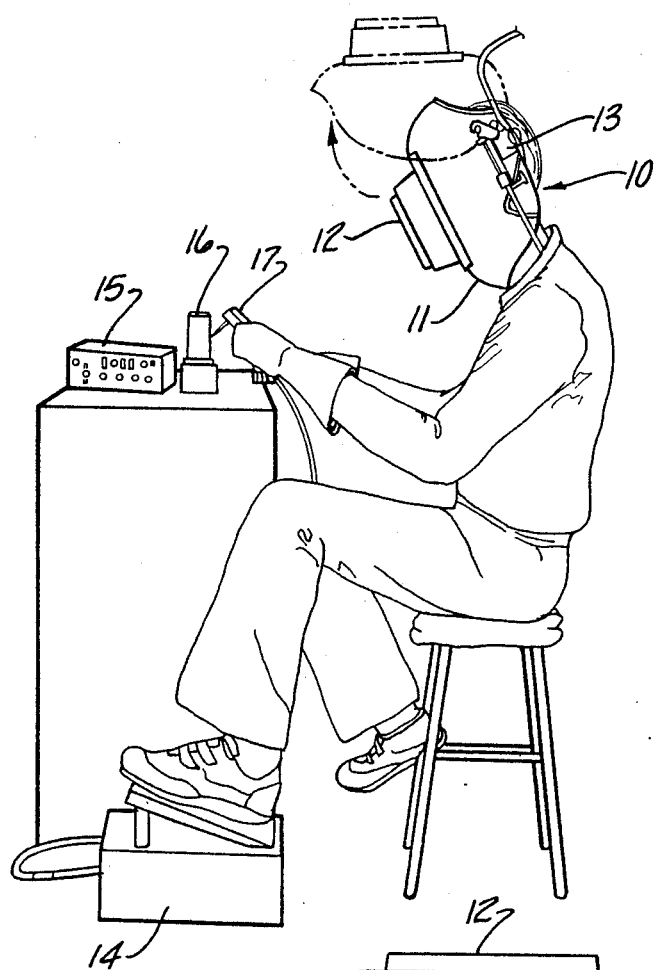
FIG. 1 is a schematic perspective of a welder practicing the present invention.
Figure 7:
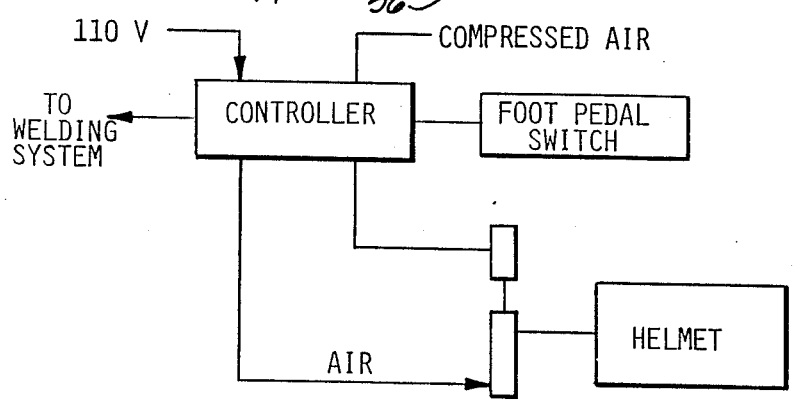
FIG. 7 is an overall schematic of the electrical and compressed air systems used in the invention.

Referring now to the figures, FIG. 1 is a general illustration of how the present invention is practiced by a welder utilizing the preferred embodiment of the invention. Shown is a welding helmet 10 of substantially conventional configuration, having a hood 11 an eye shield 12 and pivotable head band harness (not shown), having attached thereto an air powered rotation actuation means 13 a foot pedal type welding system activation switch 14 and control box 15. In practice, the welder first positions his work piece 16 and electrode holder 17 with the helmet fully raised (shown in phantom). He subsequently depresses the foot pedal switch, commencing the following sequence of events: A solenoid activated, spring biased air valve (not shown) in the control box 15 causes compressed air to be introduced into a bi-directional piston mechanism, which is a part of the rotation actuation means 13. The response of the piston causes a rotational motion in the helmet hood, thereby causing closure of the helmet over the face of the welder (as shown in the figure). A provision for a safety switch on the helmet which responds to the rotational orientation of the hood, assures welding circuit interruption unless the hood is fully down. The overall schematic interrelation between these components in shown in FIG. 7.

II. Component Description

The exact means by which the present invention accomplishes automatic rotation of the helmet may be understood by referring to FIGS. 2, 3, 4, and 5 during the description of the component parts of the invention, as follows:

A. The Pivoting Structure

A conventional arc welding helmet is utilized, having a head band 25 with pivot points on either side thereof, permitting rotational articulation, one of which being frictionally adjustable and the other modified so that a "U" shaped member 26 may fit into a slot 27 provided in helmet actuator 28. The helmet actuator, in turn, has an axially positioned cylindrical projection 29 having two parallel projections 30 extending outward therefrom. The helmet hood 31 has an aperture 32 permitting cylindrical projection 29 to extend exterior to the helmet hood, and is adapted for a close tolerant fit therewith. Exteriorly mounted on the helmet hood is a base 33 which has an aperture 34 also adapted for a close tolerant fit with the cylindrical projection 29. And finally, a cylinder actuator 35, acting as a cam, has a cylindrical axial cavity 36 having deep set slots 37 adapted to accept insertion of the end portion of the cylindrical projection 29 with its associated parallel projections 30, particularly shown in FIG. 6. A narrower axial cavity 38 extends from the surface 39 of the cylinder actuator 35 through to the cylindrically axial cavity 36 and is adapted to closely fit a pivot bolt 40 which, with washer 41, is inserted therethrough. Said helmet actuator 28 also has a similar axial cavity 42 adapted for close fitting insertion of said pivot bolt, the cavity extending completely through to the slot 27. An aperture 43 in the "U" shaped member 26 is similarly adapted to closely fit said pivot bolt when it is inserted therethrouugh. The pivot bolt 40, therefore, may be inserted through the adjacent axial cavities in the cylinder actuator 35, helmet actuator 28, and "U" shaped member 26 of the head band, and because of prior insertion of the cylindrical projection 29 through the hood aperture 32 and the base aperture 34 the said components are pivotally linked about said pivot bolt when a washer 44 and nut 45 are secured to the end thereof. It will be seen from FIG. 6 that a rotation of the cylinder actuator 35 will cause rotation of the helmet actuator 28 due to meshing of the two parallel projections 30 of the cylindrical projection 29 into the slots 37 of said cylinder actuator. Because the head band 25 is integrally connected with the "U" shaped member 26 and since the helmet actuator has a slot 27 into which said "U" shaped member inserts, rotation of the cylinder actuator 35 about the pivot bolt 40 will result in relative rotation of the head band 25 with the hood, the relative rotation being about the pivot bolt 40. In actual operation, as will be described following, it is the cylinder actuator 35, helmet actuator 28 and head band 25 that remain stationary, with the hood 31 rotating. Means to accomplish this will next be described.

B. The Base Structure

Base 33 is adapted from a flat metal piece so that when cylindrical projection 29 is inserted through aperture 34 a surface extending down to the edge of the helmet hood 46 is formed. The linear extent along said edge 46 is sufficient to establish a substantial lever arm, on the order of inches, when lips 47, preferrably three in number, project at right angles under said edge 46. Thus, the concert of action between the cylindrical projection 29 and the lips 47 cause the base 33 to be linked in positional orientation to the hood 31; a rotation of the base 33 resulting in a similar rotation of the hood 31. A projection 48 in the base 33 extends parallel to the hood edge 46 along a line above the base aperture 34, the purpose of which is to permit attachment of a compressed air activation assembly.

C. Compressed Air Activation Assembly

A commercially available compressed air activated bi-directional piston-cylinder assembly 49, for example, of the type manufactured by American Cyinder Co. of Peotome, Ill., model number 437 DBFS-2.00, is mounted to the base 33, attached to the projection thereof 48, via a ninety degree angle bracket 50. One side 51 of said bracket attaches to the projection 48 by means of an aperture 52 which is adapted to closely fit a circular projection 53 on the side of said projection 48 so that the bracket can pivot about the circular projection. The other edge 54 of the bracket is attached by screws 55 to the upper end of the cylinder housing 56. A bolt 57 with washer 58 inserts through an aperture 59 in the circular projection 53, which, via a washer 60 and nut 61, attach the bracket 50 to the base projection 48. A shaft 62 having a threaded end 63 emanates from the cylinder housing end 56 and is connected internally thereto to a bi-directional piston (not shown), which itself slidably responds to differential air pressure in said cylinder assembly 49. An aperture 64 in the attachment bracket 50 permits the shaft 62 to extend slidably outward. A threaded shaft head 65 is attached to the shaft 62 via the said screw threads. A nut 66, also adapted to screw on the threads 63, acts to tighten said shaft head 65 at a position along the threads 63 that properly adjusts the length of the shaft and head to achieve mating with the cylinder actuator 35, which itself is elongated in shape, at the end opposite to where the pivot bolt 40 attaches thereto. The shaft head 65 is apertured at 67 as is the cylinder actuator 68 permitting a shaft pivot bolt 69 with washer 70 to insert therethrough, pivotally linking the shaft to the cylinder actuator. The shaft pivot bolt 69 is held in place by a nut 71. An air hose attaches at each end of the cylinder, 72 at the upper end and 73 at the lower end thereof, providing means to introduce differential air pressure, causing motion of the internal bi-directional piston, and consequently, the shaft 62 slidably in or out of said cylinder.

The combination of the pivoting structure, base structure and compressed air activation assembly comprises the rotation actuation means, the operational interrelation of which will be next discussed.

D. The Rotation Actuation Means

Figure 2:
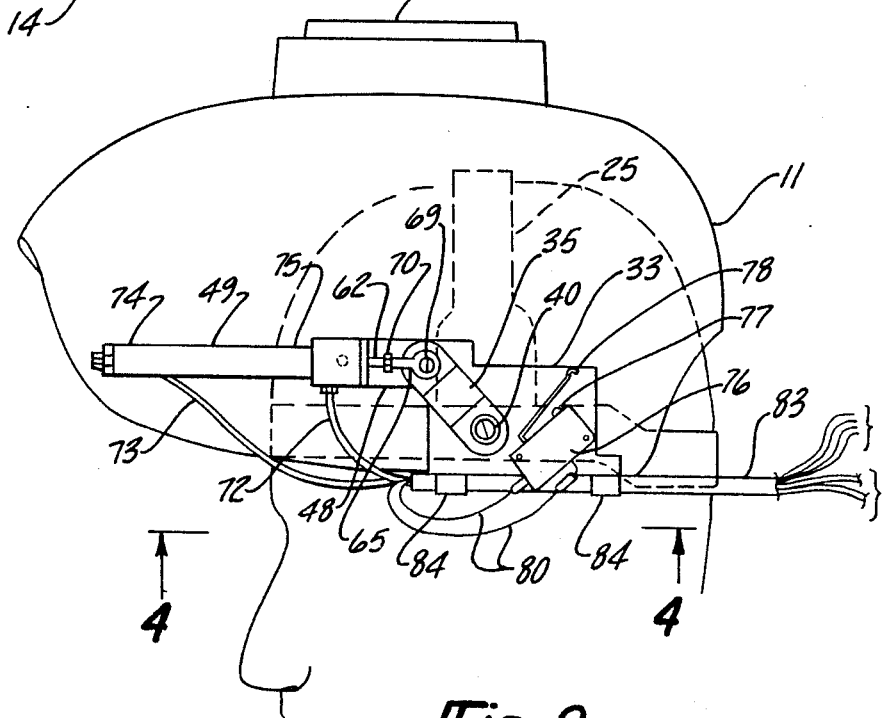
FIG. 2 is a side view of the helmet rotation actuation means, with the hood depicted in the up position.
Figure 3:
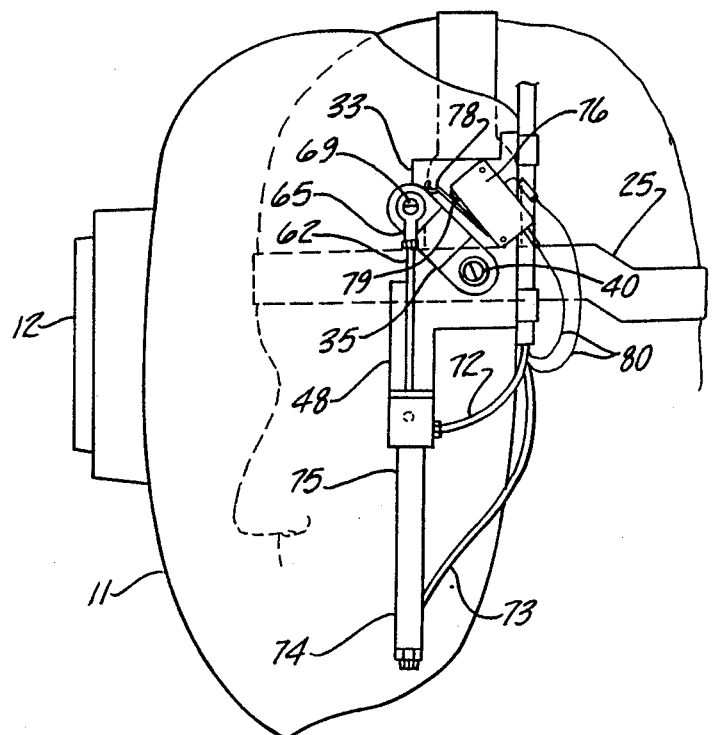
FIG. 3 is a side view of the helmet rotation actuation means, with the hood depicted in the down position.
Figure 4:
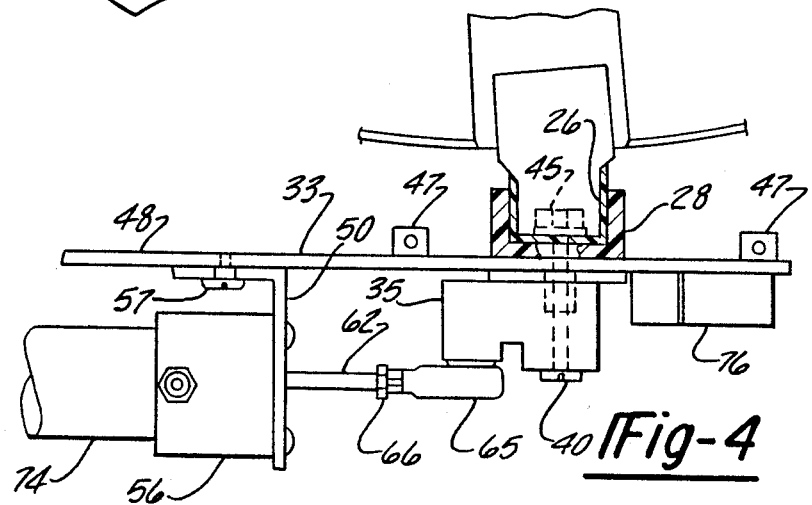
FIG. 4 is a detail of the helmet rotation actuation means along lines 4—4 in FIG. 2.

By placing the head band 25 firmly upon his head, in the hood orientation shown (up) in FIG. 2, the welder causes compressed air to enter at the cylinder lower end 74 which causes the piston to move and the shaft 62 to slide outward. This causes force to be applied to the cylinder actuator 35 which is held rigid by attachment through the aforesaid pivoting structure, to the immovable head band. Therefore, equal and opposite force is directed on the cylinder assembly 49 causing the base 33 to rotate about pivot bolt 40 due to the fact that a nonzero torque is thereby created. This torque, inducing rotary motion, has its origin in the fact that the shaft 62 does not exert force on the base 33 along a line, defined by the shaft direction going through the pivot point aperture 34, but, rather, a distance perpendicularly offset from there at aperture 59. The linear separation between these two apertures along a line perpendicular to that defined by the shaft direction, forms the lever arm over which the rotational torque is generated. Said separation is substantially on the order of an inch. Since the base plate rotates counterclockwise, similarly the hood, which is connected by lips 47 to the base, must sympathetically rotate counterclockwise. Full rotation to the down position is shown in FIG. 3. To reverse rotation, air is released from cylinder end, 74, and introduced into end, 75, thereby reversing the force, and consequent torque, causing a clockwise rotation of the base and hood to the fully up position, shown in FIG. 2.

E. The Safety Switch

A commercially available safety switch 76, for example, of the type manufactured by Cherry Switch, Inc. of Waukegon, Ill., model number V31-5-D8, is provided attached to the base 33 by screws 77 so that when the base plate rotates about pivot bolt 40 the safety switch 76 makes contact with the stationary cylinder actuator 35 through biasing lever 78. The biasing lever then depresses the switch button 79 establishing positive continuous electrical contact across the switch. Wires 80, are attached via clips 81 to external contacts 82 on the safety switch 76. A sheath 83 is provided to encase the air hoses 72 and 73 and the wires 80 precisely defining their location in the helmet vicinity via ttachments 84 to the base 33.

F. The Control Box

Figure 8:
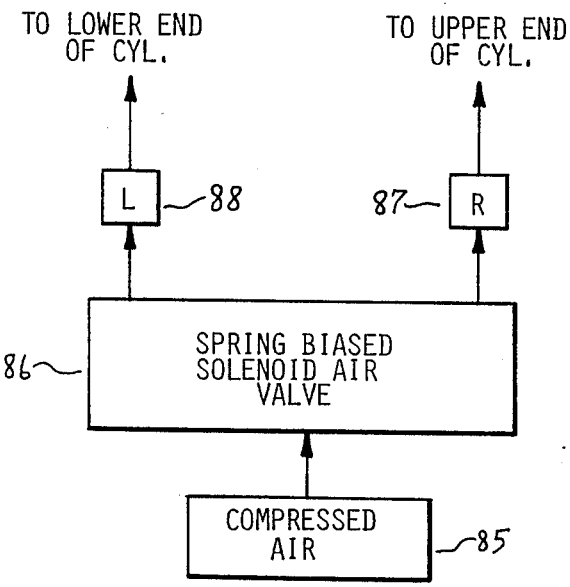
FIG. 8 is a schematic of the compressed air system.

The control box 15 contains controls for the air system, as well as the system activation switch. FIG. 8 illustrates schematically how the compressed air, generated from an external source 85, is routed to particular ends of the cylinder assembly 49. A commercially available spring biased solenoid operated air valve is employed, for example, of the type manufactured by Clippard Instrument Laboratory, Inc. of Cincinnati, Ohio, where the solenoid model number is AVSC and the attached 4-way air valve model number is MJV4, the purpose of which is to route air to the lower end of the cylinder 74 when the solenoid is electrically activated, thus lowering the hood; and in the upper end of the cylinder 75 when the solenoid is electrically deactivated, thus raising the hood. This is accomplished by means of an electrical circuit which will be described below. Commercially available air pressure regulators 87 and 88 are provided, on the control box, for each hose 72 and 73. These pressure regulators, for example, of the type manufactured by Clippard Instrument Laboratory, Inc. of Cincinnati, Ohio, model number MAR-1, control air pressure in the hoses and permit adjustment, in concert with the pivot point friction adjustment, so that a controlled, non-slamming rotational action of the hood is possible. Generally, the hose 73 controlling raising of the hood must operate at higher pressure than the hose 72 involved in lowering the hood, as the weight of the hood will impede raising, and aid in lowering, functions.

G. The Electrical Circuit

Figure 9:
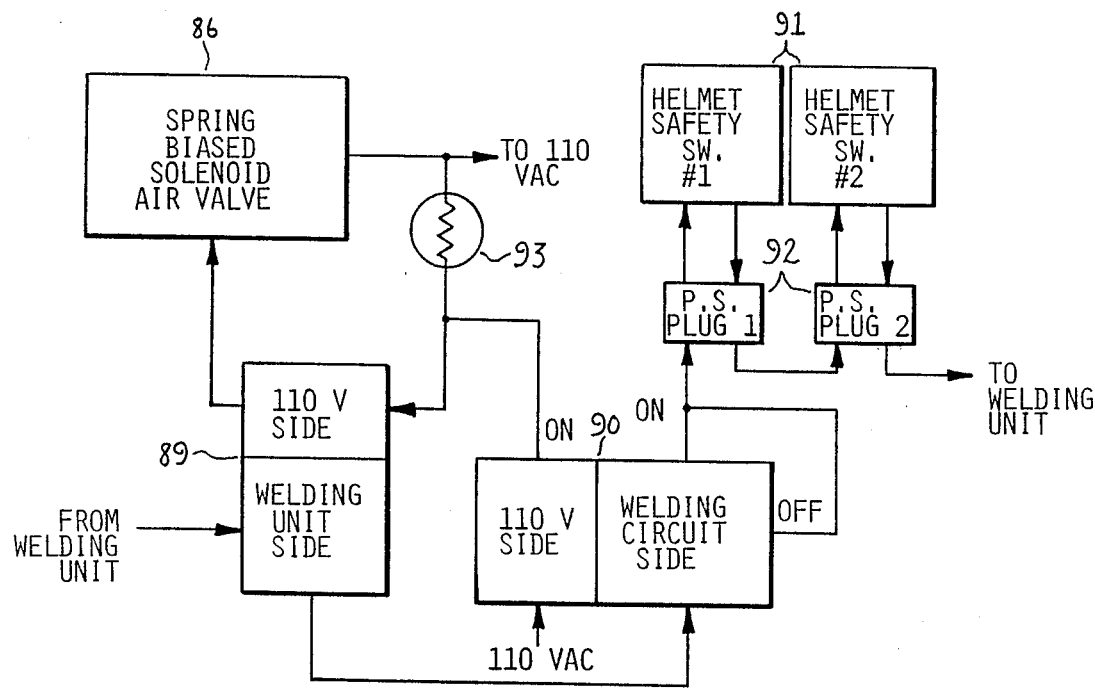
FIG. 9 is a schematic of the electrical system.

FIG. 9 illustrates schematically the electrical circuit. There are two isolated component circuits: one for the welding system and one for the air system. Each will be discussed separately.

The welding system circuit is powered from the welding apparatus and is interrupted when the spring biased welding cycle activation switch 89 is passive; when it is depressed, the circuit is active. FIG. 1 shows a foot pedal switch acting in the capacity of the welding cycle activation switch. The switch itself is a dual polarity dual throw (the other polarity being involved in the air system). The system activation switch 90, located on the control box, is a dual polarity dual throw toggle switch. When switched "on", the toggle switch routes the welding system circuit through the helmet safety switch 91. This is accomplished by inserting phone plugs, wired from the safety switch, into passive shunted plug recepticles 92 on the control box. Provision for two helmets is made, one designed for student or auxiliary use, each wired in series with the other. When the phone plugs are unplugged, the helmet safety switch (or switches in the case of dual operation) is out of the circuit. Depression of the welding cycle activation switch plus activation of the helmet safety switch (attained only when the helmet is fully down) are concurrently necessary to complete the welding system circuit and striking of an arc when the helmet is plugged in.

The air system is made active by turning the toggle type system activation switch 90 on the control box to the "on" position. A pilot light 93 will come on, indicating active connection to a source of 110 V.A.C. Depressing the welding system activation switch 89 will result in electrical current to the spring biased solenoid air valve 86 causing said air valve to direct compressed air to the lower end of the cylinder 74. Releasing the welding system activation switch results in a spring biased response in the air valve, switching compressed air to the upper end of the cylinder 75.

It will be seen that an auxiliary helmet may be added merely by plugging it in at the control box. Additionally, two forms of manual operation are possible: (1) with the toggle switch "off", and the phone plug from the helmet safety switch plugged in, the safety switch remains in the circuit, but the air system is inactive requiring manual rotation of the hood, and (2) with the toggle switch "off" and the helmet safety switch unplugged, operation is fully manual without the safety switch in the circuit.

III. Operation

In operation, the welder first adjusts the rotational action of the helmet by turning on the arc welding system (either TIG or MIG) and then the helmet system via the toggle switch at the control box, meanwhile being careful that the electrode is positioned so as to prevent the possibility of an arc striking. By alternately pressing and then releasing the spring biased welding cycle activation switch, the hood rotational action can be determined, and if necessary adjusted. Adjustment is effected by varying the air pressure in the hoses by adjusting air pressure regulators on the control box, in concert with a frictional control located at one of the pivot points of the helmet hood (on the side opposite so that where is attached the rotation actuation means). Proper adjustment will result in a controlled, smooth, non-slamming motion of the hood. Thereupon, the welder aligns and prepares the work piece and the electrode holder. This is accomplished with the hood in the fully raised position, affording the welder uncompromised vision and comfort. To begin welding, he presses the dual polarity spring biased welding cycle activation switch, which in turn, through a 110 V.A.C. electrical connection at the control box, activates the solenoid air valve, thereby sending compressed air into the lower end of the helmet mounted cylinder. The piston responds, under the urging of the air pressure, slidably outward, causing force on the connected stationary cylinder actuator cam, thereby rotating the base about its pivot, which in turn, simultaneously rotates the helmet hood downward. When the hood is in the fully down position, the cam biases the safety switch "on", thereupon completing the welding apparatus circuit and permitting the start of the electric arc cycle in the usual manner of TIG and MIG operations: flow of inert gas followed by striking of the arc. To deactivate the welding process, the welder releases the welding cycle activation switch, thereby interrupting the arc current and dectivating the solenoid current in the air valve, resulting in a spring biased response that releases air pressure in the lower end of the cylinder and introduces compressed air into the upper end of the cylinder. The piston responds slidably inward, causing the application of force on the cylinder actuator, with consequent rotation reversal of the base, and accordingly, the helmet hood. As the hood commences to rotate, biasing of the safety switch concludes, switching it "off", and preventing the striking of an arc. The hood continues to rotate until it reaches the fully raised position.

To those skilled in the art to which this invention apertains, the above described preferrd embodiment may be subject to change or modification. Such changes or modifications can be carried out without departing from the scope of the invention, which is intended to be limited only by the scope of the appended claims.

I claim:
1. An arc welding helmet for use with an arc welding system, comprising:
   a head band harness;

an arc welding helmet hood pivotally mounted to said head band harness;

an electrical activation switch; electrical circuit means interconnected with said electrical activation switch for connecting with the arc welding system;

rotation means connected with said electrical activation switch, said arc welding helmet hood and said head band harness, for automatically rotating said arc welding helmet hood relative to said head band harness responsive to actuation of said electrical activation switch, said rotation means rotating said arc welding helmet hood relative to said head band harness selectively between an up position to a down position; and safety means interconnected with said electrical circuit means and said arc welding helmet hood for permitting the arc welding system to provide an arc only when said arc welding helmet hood is located substantially at said down position.

2. The arc welding helmet of claim 1, wherein said means for automatically rotating said arc welding helmet hood relative to said head band harness comprises:

a base mounted exteriorly to said arc welding helmet hood;

a compressed air activted, bi-directional piston-cylinder assembly, said bi-directional piston-cylinder assembly having a shaft extending therefrom;

control box means connected with said electrical circuit means and said bi-directional piston-cylinder assembly for regulating compressed air to said bi-directional piston-cylinder assembly responsive to actuation of said electrical activation switch;

a cylinder actuator pivotally connected to said base, said cylinder actuator being connected at one end thereof to said shaft, wherein linear movement of said shaft in response to activation of said bi-directional piston-cylinder assembly induces rotational movement of said cylinder actuator means about an axis;

a helmet actuator connected with said cylinder actuator in a fixed rotative relationship with respect thereto, said helmet actuator further being connected with said head band harness in a fixed rotative relationship with respect thereto; and, pivot means connected with said base for providing pivotal movement of said cylinder actuator and said helmet actuator about said axis;

whereby, when said electrical activation switch is actuated, said arc welding hood is caused to rotate from said up position to said down position, and when said electrical activation switch is thereafter no longer actuated, said arc welding hood is caused to rotate from said down position to said up position.

3. The arc welding helmet of claim 2, wherein said safety means comprises:

an electrical switch, connected with said electrical circuit means, said electrical switch being mounted in cooperating engagement between said cylinder actuator and said base so that said electrical switch is actuated only when said arc welding helmet hood has been pivotally rotated into said down position, the arc welding system providing an arc only when said electrical switch is actuated.

4. An arc welding helmet for use with an arc welding system, said arc welding helmet comprising:

a head band harness;

an arc welding helmet hood pivotally mounted to said head band harness, said arc welding helmet hood being selectively rotatable between an up position and a down position;

a base mounted exteriorly to said arc welding helmet hood;

rotation means connected with said base for automatically rotating said arc welding helmet hood relative to said head band harness between said up position and said down position; and, electrical switch means for being connected with said arc welding system, said electrical switch means being mounted in cooperating engagement between said rotation means and said base so that said electrical switch means is actuated only when said arc welding helmet hood has been pivotably rotated into said down position, the arc welding system providing an arc only when said electrical switch means is actuated.

5. The arc welding system of claim 2, wherein said control box means regulates speed of movement of said bi-directional piston-cylinder.

6. The arc welding system of claim 3, wherein said control box means regulates speed of movement of said bi-directional piston-cylinder.

* * * * *